(12) United States Patent
Bausch et al.

(10) Patent No.: US 6,299,906 B1
(45) Date of Patent: Oct. 9, 2001

(54) PROCESS FOR MAKING SUBMICRON PARTICLES

(75) Inventors: Alexander Bausch, Lörrach (DE); Pirmin Hidber, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/287,409

(22) Filed: Apr. 6, 1999

(30) Foreign Application Priority Data

Apr. 9, 1998 (EP) .................................. 98106534

(51) Int. Cl.[7] .............................. A61K 9/14; A61K 31/47
(52) U.S. Cl. ..................... 424/489; 514/311; 514/314; 424/490; 424/497
(58) Field of Search .................... 424/489, 490, 424/497; 514/311, 314

(56) References Cited

U.S. PATENT DOCUMENTS

| | | |
|---|---|---|
| 3,998,753 | 12/1976 | Antoshkiw et al. . |
| 4,734,227 | 3/1988 | Smith . |
| 5,170,727 | * 12/1992 | Nielsen . |

FOREIGN PATENT DOCUMENTS

| | | |
|---|---|---|
| 95/21688 | 8/1995 | (WO) . |
| 97/14407 | 4/1997 | (WO) . |
| 98/16204 | 4/1998 | (WO) . |

OTHER PUBLICATIONS

Donsi, G., et al., Pharm. Acta. Helv., vol. 66, No. 5–6, 1991, pp. 170–172.

Bala Subramaniam et al., Journal of Pharmaceutical Sciences, "Pharmaceutical Processing with Supercritical Carbon Dioxide", 86(8):885–890 (Aug. 1997).

Heinz Sucker et al., Pharmazeutische Technologie, Edition 2, Georg Thiem Verlag, Stuttgart/New York, pp. 419–424 (1991).

Hans Steffen, BT Gattefossé No. 81, "Controlled Precipitation—A Method to Produce Small Drug Particles and to Increase Bioavailability", p. 45–53 (1988).

* cited by examiner

Primary Examiner—Gollamudi S. Kishore
Assistant Examiner—Amy E Pulliam
(74) Attorney, Agent, or Firm—George W. Johnston; William H. Epstein; Arthur D. Dawson (57) ABSTRACT

The present invention relates to a process for manufacturing a pulverous preparation of a submicron-sized biologically active compound comprising the steps of dissolving a biologically active compound under elevated pressure in a compressed gas, liquid or supercritical fluid containing a surface modifier; and rapidly expanding the compressed solution thereby precipitating the dissolved compound. An alternative process comprises dissolving the biologically active compound in compressed dimethylether, which may optionally contain a surface modifier; and spraying the compressed solution into an antisolvent phase, optionally containing a surface modifier, under vacuum, atmospheric pressure or elevated pressure. An optional third step involves converting the antisolvent phase into a pulverous preparation using conventional powder processing.

14 Claims, 3 Drawing Sheets

PROCESS FOR MAKING SUBMICRON PARTICLES

FIELD OF THE INVENTION

The invention provides a novel process for producing submicron-sized particles of a biologically active compound or pharmaceutical.

A number of different processes to produce very small particles of a pharmaceutical have been described. (e.g. Rapid Expansion (of) Supercritical (fluid) Solution (RESS), Gas Antisolvent (GAS), Particles (from) Gas Saturated Solution (PGSS), Supercritical Anti-Solvent (PRECIPITATION) (SAS)). These processes are described in Journal of Pharmaceutical Sciences Vol. 86, No. 8, August 1997, pp. 885–890 under the title "Pharmaceutical Processing with Supercritical Carbon Dioxide. Typically the drug is dissolved in a compressed gas and subsequently rapidly expanded mostly into atmospheric pressure. Due to the expansion conditions and to a high surface energy in the gas very small particle sizes, i.e., smaller than 1 $\mu$m are hard to achieve and to handle. It is well known that such high surface energy can only be handled by using a surface modifier to decrease the surface energy, to achieve stabilization of small particles in suspension. H. Sucker, P. Fuchs, P. Speiser, "Pharmazeutische Technologie",2. Edition, 1991, Georg Thieme Verlag, Stuttgart/New York, pp 419–424; and Hans Steffen, BT Gattefossé No. 81, 1988, pp. 45–53, "Controlled Precipitation—a Method to Produce Small Drug Particles and to Increase Bioavaibility".

International application WO 97/14407 describes a supercritical fluid/compressed fluid based process to produce submicron-sized particles of biologically active compounds, which process comprises the steps of:

(1) dissolving a water insoluble biologically active compound in a solvent thereof;

(2) spraying the solution of step (1) into a compressed gas, liquid or supercritical fluid in the presence of a surface modifier dispersed in an aqueous phase.

In another embodiment the process described in WO 97/14407 comprises the steps of:

(1) dissolving a water insoluble biologically active compound in a compressed fluid;

(2) spraying the compressed fluid of step (1) into an aqueous phase containing a surface modifier.

The process described in WO 97/14407 may be difficult to realise on an industrial scale for various reasons. On an industrial scale it is difficult to reach a uniform distribution of temperature in the connection tubes. Due to such variations in temperature, aggregation or flocculation of particles dissolved in the supercritical solution may occur causing clogging of the tubes or spraying-nozzles.

The solubility of most of the pharmaceutical compounds in liquid or supercritical $CO_2$ is very low even under high pressure. Therefore the use of additional cosolvents is proposed. Most of these cosolvents are liquids under atmospheric pressure. By spraying the solution containing the pharmaceutical into the liquid phase, e.g. aqueous phase, the fraction of the cosolvent in the liquid phase increases. Therefore, the solubility of the compound in the liquid phase also increases. This can destabilize the suspension on an industrial scale.

In addition, the recycling of the pressurized gas becomes more difficult and expensive using a cosolvent.

A pressurised gas with high solubility for pharmaceutical compounds would allow the process to be effected without the use of cosolvents.

SUMMARY OF THE INVENTION

The object of the present invention is thus to provide a novel process for producing submicron-sized particles of a biologically active compound from a compressed gas, liquid or supercritical fluid, thus avoiding the above mentioned difficulties.

The process of the present invention is based on the use of compressed gas and fluids including supercritical technology yielding submicron-sized particles having a narrow size distribution and being stabilized by a surface modifier.

The process can be performed either batchwise or continuously and is applicable to a wide range of substances.

In a first aspect of the invention it has now been found that the above mentioned problems concerning the cosolvent can be avoided by using compressed dimethylether to solvate the biologically active compound.

In a second aspect of the invention it has now been found that the above mentioned problems of clogging can be avoided by stabilizing the supercritical solution by adding a surface modifier in the compressed gas solution.

The invention thus concerns a process for the manufacture of a pulverous preparation of a submicron-sized biologically active compound comprising as a first step, dissolving a biologically active compound under elevated pressure in a compressed gas, liquid or supercritical fluid containing a surface modifier. Alternatively, the biologically active compound may be dissolved in compressed dimethylether, which may optionally contain a surface modifier. The second step of the process comprises rapidly expanding the compressed solution of step (1) thereby precipitating the dissolved compound. Alternatively, the second step comprises spraying the compressed solution of step (1) into an antisolvent phase, which may optionally contain a surface modifier, under vacuum, atmospheric pressure or elevated pressure. A third step, which is optional, comprises converting the antisolvent phase into a pulverous preparation using conventional powder processing techniques.

Conventional powder techniques are for example spray drying and freeze drying.

In this manner the formation of submicron sized particles stabilized by a surface modifier is achieved.

The term "submicron-sized particles" embraces particles having a median diameter (Dv 0.5) within the range of 5 nm to 5 $\mu$m, preferably 200 nm to 1 $\mu$m.

In cases where the compressed fluid is compressed dimethylether, the use of surface modifier is optionally and can be added to the compressed fluid (step 1) or to the antisolvent phase.

However, where the compressed fluid is not dimethylether, a surface modifier must be added to the compressed fluid.

The term "surface modifier" in step (1) and in the antisolvent phase of the present process embraces common modifiers as described in "Pharmazeutische Technologie, 4. Edition, 1993, Georg Thieme Verlag Stuttgart, N. Y."

Examples of suitable surface modifiers are: natural surfactants such as e.g. gelatine, paraffin, cholesterol esters and triglycerides; non-ionic surfactants such as e.g. polyethylene glycol; anionic surfactants such as e.g. natrium dodecylsulfate; cationic surfactants such as e.g. quaternary ammonium compounds; block copolymers of ethylene oxide and propylene oxide available from BASF under the trade name Pluronic®; olyoxamines availaible under the tradename Tetronic ®; polyoxyethylen sorbian fatty acid esters, e.g.

Tween 20, 40, 60 and 80; Klucel EF, Eudragit E, Arlactel 40, Carbopol 940, PVP K50; Brij 96 and Aerosol OT®.

Preferred surface modifiers are Brij 96® (polyethyleneglycolether of lauryl,-cetyl-, stearyl- and oleylalcohols, available from Atlas Chemie) and Aerosol OT® (sodium di-isooctylsulphosuccinate availaible from Wako Junyaku Corp).

In step (1) and in the antisolvent phase and the same modifier can be used.

As shown by H. Steffen (BT Gattefossé No. 81, 1988, pp. 45–53) the concentration of the surface modifier depends on the critical micelle concentration (CMC). The amount of surface modifier needed depends therefore on the CMC and the surface area of the particles.

The addition of a surface modifier to the compressed gas prior to the spraying has the advantage that (i) nuclei and particles formed spontaneously in the pipes or—due to the pressure drop—in the region of the nozzle are immediately stabilized and their growth is hindered further, thereby preventing clogging, (ii) the mixing of the precipitated particles and the surface modifier is improved by simultaneously spraying the solution of the drug and the surface modifier through the same nozzle, (iii) the use of an antisolvent phase which neither solubilizes the drug nor the surface modifier is allowed.

Due to the presence of a surface modifier in the compressed gas, liquid or supercritical liquid the following advantages are achieved:

Differences in the pressure and temperature are counteracted by stabilizing any nuclei formed.

The pressure drop in the region of the nozzle can be accommodated without clogging.

The surface modifier is located very close to the region of particle formation and not distributed in the whole liquid.

It is possible to expand into a liquid phase, e.g. compressed $CO_2$, which is then evaporated by keeping the stabilization of the suspension. Thus, the additional step of spray drying is no longer necessary.

The term "compressed gas, liquid or supercritical fluid" embraces dimethylether, carbon dioxide, straight chain or branched C1–C6-alkanes or combinations thereof. Examples for said alkanes are ethane, propane, butane and isopropane and the like.

The term "biologically active compound" includes, but is not limited to pharmaceuticals such as those listed below:

| therapeutic category | INN (international non-proprietary name) |
|---|---|
| anxiolytic | Diazepam, Bromazepam |
| antidepressant | Moclobemide |
| anesthetic | Midazolam |
| antiviral | Ganciclovir, Zalcitabine, Nelfinavir mesylate |
| proteinase inhibitor | Saquinavir, Nelfinavir |
| anti-inflammatory | Naproxen, Tenoxicam, Ketorolac |
| antibacterial | Ceftriaxone, Timethoprim, Sulfamethoxazol. |
| antimalarial | Mefloquine |
| antihypertensive | Cilazapril |
| antiseborrheic | Isotretinoin |
| calcium regulator | Calcitriol |
| lipase inhibitor | Orlistat |

-continued

| therapeutic category | INN (international non-proprietary name) |
|---|---|
| antiparkinson | Tolcapone |
| antiarthritic | Mycophenolate mofetil |
| antithrombotic | Lamifiban |
| endothelin antagonist | Bosentan |

The antisolvent can be any solvent wherein the pharmaceutical is poorly soluble. For example the antisolvent can be water or compressed $CO_2$.

The temperature in step (1) or in the antisolvent phase is each independently in the range of 0–250° C., preferably 20–60° C.

The pressure in step (1) is $2–500\times10^5$ Pa, preferably $2–300\times10^5$ Pa and the pressure in the antisolvent phase is $0.05–500\times10^5$ Pa, preferably $1–200\times10^5$ Pa, most preferably $3–100\times10^5$ Pa.

Preferably the pressure in step (1) and in the antisolvent phase is not the same. The pressure difference is used to control the particle size.

BRIEF DESCRIPTION OF THE DRAWINGS

FIG. 1 is a schematic representation of an apparatus for carrying out the present invention.

FIG. 2 and FIG. 3 show the particle size distribution of the same suspension but using different methods to determine the particle size distribution.

FIG. 2 shows the particle size distribution of Saquinavir using Photon Correlation Spectroscopy (batch no. 1051/30); Rec 7; Angle 90; KCps 931.3; ZAve 254.7; Poly 0.031; Multi Angle.

FIG. 3 shows particle size distribution of Saquinavir using Laser Diffraction (batch no. 1051/30); modifier Aerosol OT; dimethylether; focus 50 mm.

DETAILED DESCRIPTION OF THE INVENTION

Referring to FIG. 1, a 6 liter high pressure vessel, also referred to as dissolution unit (3) for dissolving the drug substance, and optionally the surface modifier, was connected via an outlet tube to a 4 liter high pressure vessel (8) which was used as the precipitation unit. The dissolution unit (3) was equipped with a container (4) closed with two sinter plates (5) which retained the solid drug substance, and if present the solid surface modifier, but allowed free flow of the compressed fluid, and optionally surface modifier, or compressed fluid containing drug. A bypass line (1) allowed pre-pressurization the precipitation unit (8). The temperature of the two vessels (3) and (8) was controlled independently of each other by two thermostats TC1 and TC2. All pipes were heated by heating tape. The pressure in the two vessels (3, 8) was controlled using two pressure regulators (7, 10). The flow rate through the nozzle (9) was measured with a flow meter (11). The expansion nozzle included a 1.5 mm thick, 0 lmm diameter laser drilled orifice. The downstream end of the orifice was counterbored into a V-shape.

A typical experiment consisted of:

(i) charging the container (4) with the desired amount of drug substance and, optionally, surface modifier, (ii) closing the container with the sinter plates (5) and putting it into vessel, (iii) adding the antisolvent, optionally together with surface modifier, to the precipitation unit (8), (iv) pressurising the two vessels (3) and (8) to the desired pressure levels, and (v) thermostating the vessels and the pipes to the desired temperature levels.

The whole system was equilibrated for 90 min, after which the spraying process was started by pumping additional compressed fluid into vessel (3). The increase of the pressure in the dissolution chamber (3) forced the pressure regulator (7) to open the valve to the spraying unit thereby starting the spraying. The differential pressure between the first (3) and second (8) vessel was controlled by a pressure regulator (10). The flow rate through the nozzle (9) was controlled by adjusting the pump flow rate (2). During the whole experiment, temperature and pressure in the two vessels (3, 8) were monitored constantly.

A continuous process can be achieved by continuous, controlled feeding of drug substance, and optionally surface modifier, into the dissolution unit (3), dissolving it in the compressed fluid and spraying the solution into the antisolvent phase in the precipitation unit (8). Suspension is continually removed from the precipitation unit and replaced by new antisolvent, optionally containing surface modifier.

Figure 2:
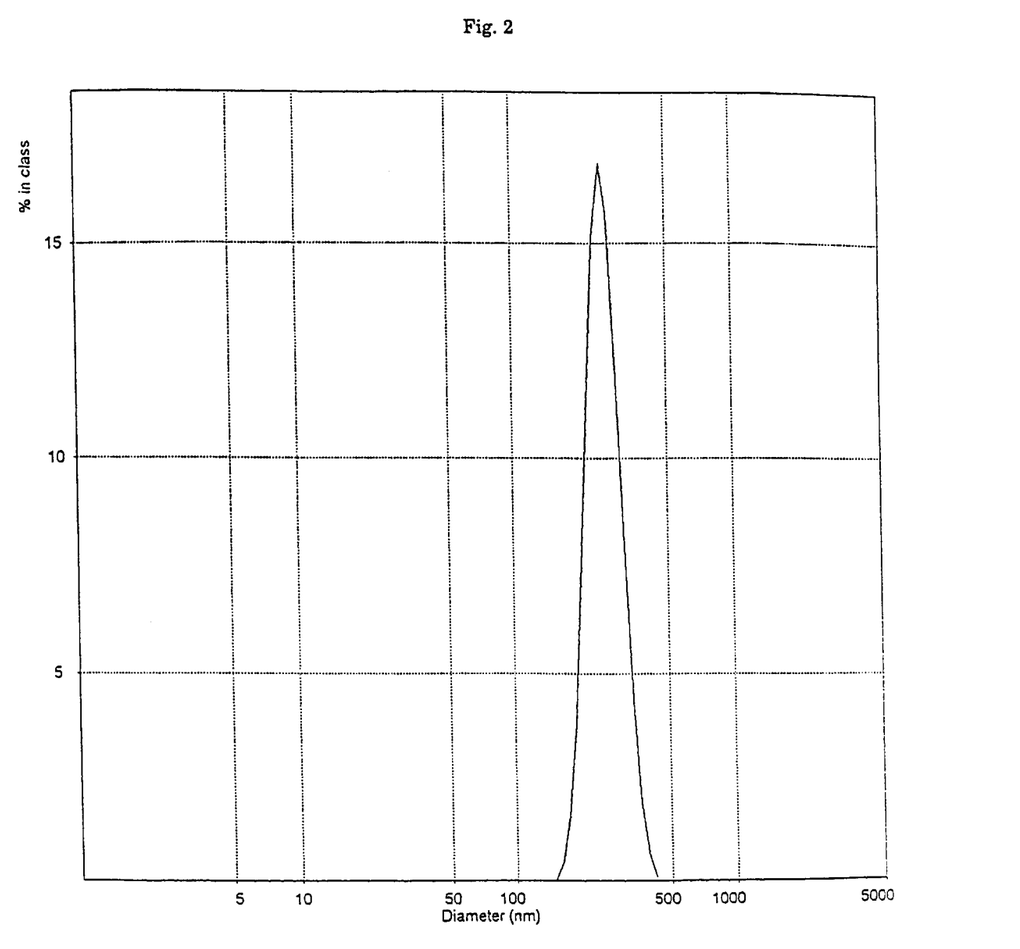
Figure 3:
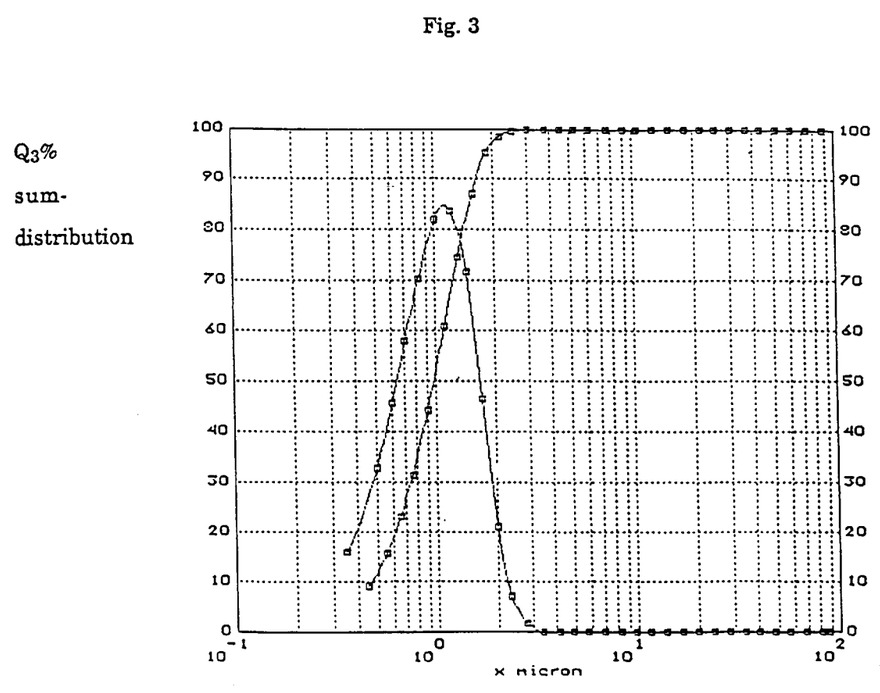

The particle size distribution of very small particles of approximately 1 μm is difficult to determine accurately. Two commonly used methods are photon correlation spectroscopy (PCS) and laser diffraction. Photon correlation spectroscopy is commonly used for characterization of submicron suspensions and emulsions. Due to the principle of the measurement, movement of particles, particles larger than 3 to 5 μm cannot be seen with this method. With laser diffraction small particles, >0.1 μm, as well as larger particles, up to 2 mm, can be characterized in parallel. The diffraction of the light is thereby measured at small diffraction angles. For very small particles the method tends to overestimate the particle size due to transmission of light through the particles. This effect of over- and underestimation of the particle size by the two methods is demonstrated in FIG. 2 and FIG. 3, showing the particle size distribution of the same suspension, measured with PCS (FIG. 2), and with laser diffraction (FIG. 3).

To assess the performance of a process for the formation of submicron-sized particles, it is important to show that, besides the fine particles, no fractions of large particles are formed. Formation of fractions of coarse particles was observed especially after clogging of the nozzle, e.g. expansion of a compound dissolved in a compressed gas without modifier. To be able to detect the presence of coarse particles, laser diffraction was chosen to characterize the whole suspension. With its wide dynamic range, laser diffraction allows the detection of particles up to 2 mm that cannot be seen by the PCS method. Since laser diffraction tends to overestimate the particle size (FIGS. 2, 3), all the particle sizes determined by laser diffraction can be considered as too large. Nevertheless laser diffraction proved to be sensitive enough to show the influence of different process parameters on the particle size.

The following Examples explain the invention in more detail, without limiting the scope thereof.

EXAMPLE 1

Solubilities of Pharmaceutical Drug Substances in Liquid Carbon Dioxide and Dimethyl Ether A comparison of solubilities of a number of pharmaceutical drug substances was performed as follows:

Approximately 3–5 g of the drug product was slightly compressed in a uniaxial press to avoid the formation of a stable suspension. The so compressed powder was placed in a pressure chamber with a sapphire glass (30 ml volume). The temperature of the pressure chamber was controlled by water bath. Then the pressure in the chamber was increased using the corresponding gas and equilibrated for 1–3 hours. After equilibration a 1.0 ml sample was drawn under constant pressure and temperature conditions using a high pressure line with a defined volume. This sample was expanded into a liquid with a good solubility for the respective compound. The sample container was afterwards rinsed with the same liquid to collect the residues of the substance in the sample container.

The solubility (G/V) was determined either by HPLC or gravimetrically after removing the liquid, and is shown in Table 1.

TABLE 1

Solubilities of pharmaceutical drug substances in liquid carbon dioxide and dimethyl ether

| Drug substance | solubility ($CO_2$) [%(g/V)] | Conditions [20 C./bar] | solubility (DME) [%(g/V)] | conditions [20 C./bar] |
|---|---|---|---|---|
| Orlistat (THL) | 0.6 | 30° C./100 bar | 17.8 | 20° C./4.5 bar |
| Isotretionin | 0.3 | 45° C./200 bar | 6.0 | 45/200 bar |
| Sulfamethoxazol | 0.1 | 45° C./140 bar | 5.4 | 45° C./140 bar |
| Saquinavir | <0.1 | 45° C./200 bar | >10 | 25° C./100 bar |
| Diazepam | 0.15 | 45° C./200 bar | >10 | 45° C./200 bar |
| Moclobemide | 0.35 | 45 °/200 bar | 3.7 | 45° C./200 bar |
| Bosentan | <0.1 | 45° C./200 bar | 9.0 | 45° C./200 bar |

EXAMPLE 2

Expansion of Orlistat (Tetrahydrolipstatin THL)— Influence of the Spraying Time 150 g of solid THL and 75 g Brij 96 in a container with two sinter plates was charged into an autoclave having a volume of 6 liter. The autoclave was kept at a temperature of 40° C. with a water bath. Then the autoclave was filled with $CO_2$ up to a pressure of 200 bar and equilibrated for 90 min.

The autoclave was connected to a second autoclave via a heated high pressure line, kept at 40° C. This second autoclave had a volume of 4 liter. The dissolved THL was sprayed into 1.25 liter of an aqueous solution of Brij 96 (0.06%=1 CMC) in this second autoclave. The pressure of the first autoclave was kept constant at 200 bar by pumping in additional gas.

Several trials spraying a solution of THL in $CO_2$ without surfactant into an aqueous solution with various concentrations of Brij 96 was not successful due to clogging of the nozzle. The small amount of surfactant (1 CMC) was not added for stabilization.

After 90, 150, and 180 minutes of spraying, a sample for particle size distribution was drawn. After 180 min the whole amount of THL/Brij was removed from the first container (≈12% THL in the final suspension). Based on this result, a solid concentration of 5–8% should be achievable in production scale.

As listed in Table 2 below, the resulting particle size distribution of THL was kept almost constant over the whole trial. This shows that stabilization of the nuclei with the surfactant was very effective up to a high solid concentration.

TABLE 2

Particle size distributions determined with laser diffraction.

| Spraying Time | Dv 0.1 [μm] | Dv 0.5 [μm] | Dv 0.9 [μm] |
|---|---|---|---|
| 90 min | 0.6 | 1.4 | 2.9 |
| 150 | 0.4 | 1.5 | 3.5 |
| 180 | 0.9 | 2.1 | 4.5 |

EXAMPLE 3

Expansion of Saquinavir—Influence of the Pressure in the First Container on the Resulting Particle Size 50 g of solid Saquinavir and 25 g Aerosol OT in a container with two sinter plates was charged into an autoclave having a volume of 6 liter. The autoclave was kept at a temperature of 40° C. with a water bath. Then the autoclave was filled with DME up to different pressures and equilibrated for 90 min.

The autoclave was connected to a second autoclave via a heated high pressure line, kept at 25° C., 5 bar. This second autoclave had a volume of 4 liter. The dissolved Saquinavir/Aerosol OT was sprayed into a second autoclave filled with 1.2 liter of pure water. The pressure of the first autoclave was kept constant by pumping in additional gas.

Several trials spraying a solution of Saquinavir in DME without surfactant into an aqueous solution with various concentrations of surfactant was not successful due to clogging of the nozzle.

After 20 min spraying a sample for particle size distribution was determoined to be about 4% Saquinavir in the final suspension.

The resulting particle size distribution of Saquinavir could be controlled by the pressure applied in the first container as shown in Table 3 below. This shows that as theoretically proposed the supersaturation can be kept constant during the process and correlates with the resulting particle size. Also the stabilization of the nuclei with the surfactant was effective.

The nozzle diameter was 0.1 mm. As commonly known a further decrease of particle size can be obtained by decrease of the nozzle diameter.

TABLE 3

Particle size distributions determined with laser diffraction.

| Pressure | Dv 0.1 [μm] | Dv 0.5 [μm] | Dv 0.9 [μm] |
|---|---|---|---|
| 50 bar | 0.5 | 3.8 | 6.4 |
| 100 bar | 1.0 | 2.1 | 4.5 |
| 200 bar | 0.9 | 1.5 | 2.4 |
| 280 bar | 0.4 | 0.8 | 1.7 |

EXAMPLE 4

Expansion of Saquinavir—Influence of the Surfactant 50 g of solid Saquinavir and 5 g Brij 96 in a container with two sinter plates was charged into an autoclave having a volume of 6 liter. The autoclave was kept at a temperature of 40° C. with a water bath. Then the autoclave was filled with DME up to 200 bar and equilibrated for 90 min.

The autoclave was connected to a second autoclave via a heated high pressure line, kept at 25° C., at 5 bar. This second autoclave had a volume of 4 liter. The dissolved Saquinavir/Brij 96 was sprayed into a second autoclave filled with 1.2 liter of pure water. The pressure of the first autoclave was kept constant by pumping in additional gas.

After 20 minutes of spraying, a sample for particle size distribution was determined to be about 4% Saquinavir in the final suspension.

The resulting particle size distribution of Saquinavir stabilized with Brij 96, a non-ionic surfactant, was comparable with the results obtained with Aerosol OT, an ionic surfactant (see Example 3).

TABLE 4

Particle size distributions determined with laser diffraction.

| Surfactant | Dv 0.1 [μm] | Dv 0.5 [μm] | Dv 0.9 [μm] |
|---|---|---|---|
| Aerosol OT | 0.9 | 1.5 | 2.4 |
| Brij 96 | 0.7 | 1.4 | 3.0 |

What is claimed is:

1. A process for the manufacture of a pulverous preparation of a submicron-sized particulate Saquinavir comprising the steps of:
   (1) dissolving Saquinavir under an elevated pressure in dimethyl ether in a supercritical stat of temperature and pressure containing a surface modifier; and
   (2) rapidly expanding the compressed solution of step (1) thereby precipitating the dissolved Saquinavir as discrete submicron particles.

2. A process according to claim 1 further comprising maintaining the temperature in step (1) or (2) each independently in the range of 0–250° C.

3. A process according to claim 2, further comprising maintaining the temperature in step (1) or (2) each independently in the range between about 20–60° C.

4. A process according to claim 1 further comprising maintaining the pressure in step (1) between about 2–500× $10^5$ Pa, and maintaining the pressure in step (2) lower than said pressure in step (1) thereby forming a pressure differential, said pressure differential being selected for providing a preselected size distribution of said particles being formed.

5. A process according to claim 4, wherein the pressure maintained in step (1) is between about 2–300× $10^5$ Pa and the pressure maintained in step (2) is between about 1–200× $10^5$ Pa.

6. A process according to claim 4, wherein the pressure in step (2) is maintained between about 3–100× $10^5$ Pa.

7. A process according to claim 1, further comprising selecting said surface modifier from the group consisting of a polyethyleneglycolether of lauryl,-cetyl-, stearyl- or oleylalcohols and sodium di-isooctylsulphosuccinate.

8. A process according to claim 1, wherein precipitating the particles step results in particles having a median diameter (Dv 0.5 of between about 5 nm to 5 μm, preferably between about 200 nm to 1 μm.

9. A process according to claim 8, further comprising precipitating particles having a median diameter (Dv 0.5 of between about 200 nm to 1 μm.

10. A process according to claim 1, wherein said rapidly expanding step further comprises spraying the compressed solution of Saquinavir into an antisolvent phase thereby forming discrete submicron particles of Saquinavir.

11. A process according to claim 1, wherein the antisolvent phase water and the pulverous preparation is obtained by separating the discrete submicron Saquinavir particles from the antisolvent.

12. A process according to claim 1, further comprising performing the process batchwise.

13. Continuously performing said process of claim 1, comprising the steps of:
  (1) feeding Saquinavir and a sufficient quantity of a surface modifier into a dissolution unit containing dimethyl ether in a supercritical state of temperature and pressure;
  (2) dissolving said Saquinavir in the supercritical dimethyl ether in said dissolution unit and spraying said solution into an antisolvent water phase in a precipitation unit maintained at a lower pressure than the pressure in said dissolution unit thereby forming discrete submicron particles of Saquinavir suspended in the water phase;
  (3) continually removing the suspension of discrete submicron Saquinavir particles in water from the precipitation unit and replacing the suspension by fresh antisolvent water; and
  (4) separating said discrete submicron Saquinavir particles from the water.

14. A pharmaceutical preparation containing a pharmaceutically effective amount of particulate Saquinavir prepared by the process according to claim 1.

* * * * *

UNITED STATES PATENT AND TRADEMARK OFFICE
CERTIFICATE OF CORRECTION

PATENT NO.     : 6,299,906 B1
DATED          : October 9, 2001
INVENTOR(S)    : Alexander Bausch et al.

It is certified that error appears in the above-identified patent and that said Letters Patent is hereby corrected as shown below:

Title page,
The title page should be deleted and substitute therefore the attached Title page.

Figure 1:
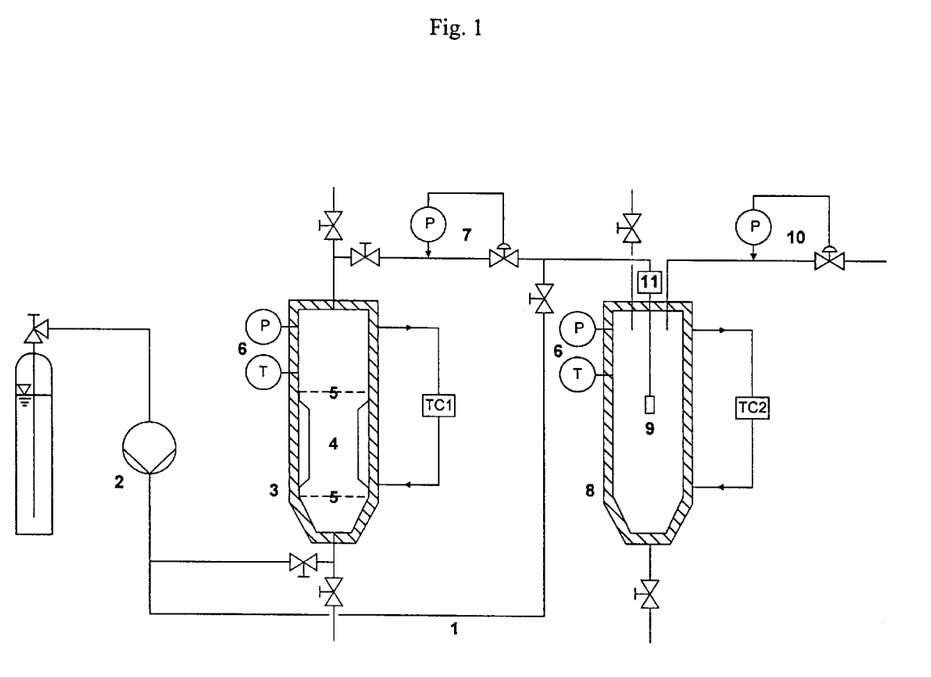

Drawings,
Delete Drawing Sheets 1-3, and substitute therefore the Drawing Sheets, consisting of Figs. 1-3, as shown on the attached pages.

Signed and Sealed this

Twenty-fifth Day of June, 2002

Attest:

Attesting Officer

JAMES E. ROGAN
Director of the United States Patent and Trademark Office

(12) United States Patent
Bausch et al.

(10) Patent No.: US 6,299,906 B1
(45) Date of Patent: Oct. 9, 2001

(54) PROCESS FOR MAKING SUBMICRON PARTICLES

(75) Inventors: Alexander Bausch, Lörrach (DE); Pirmin Hidber, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/287,409

(22) Filed: Apr. 6, 1999

(30) Foreign Application Priority Data

Apr. 9, 1998 (EP) .................................................. 98106534

(51) Int. Cl.$^7$ ............................ A61K 9/14; A61K 31/47
(52) U.S. Cl. ........................ 424/489; 514/311; 514/314; 424/490; 424/497
(58) Field of Search .................................. 424/489, 490, 424/497; 514/311, 314

(56) References Cited

U.S. PATENT DOCUMENTS

| | | |
|---|---|---|
| 3,998,753 | 12/1976 | Antoshkiw et al. |
| 4,734,227 | 3/1988 | Smith. |
| 5,170,727 | * 12/1992 | Nielsen. |

FOREIGN PATENT DOCUMENTS

| | | |
|---|---|---|
| 95/21688 | 8/1995 | (WO). |
| 97/14407 | 4/1997 | (WO). |
| 98/16204 | 4/1998 | (WO). |

OTHER PUBLICATIONS

Donsi, G., et al., Pharm. Acta. Helv., vol. 66, No. 5–6, 1991, pp. 170–172.
Bala Subramaniam et al., Journal of Pharmaceutical Sciences, "Pharmaceutical Processing with Supercritical Carbon Dioxide", 86(8):885–890 (Aug. 1997).
Heinz Sucker et al., Pharmazeutische Technologie, Edition 2, Georg Thiem Verlag, Stuttgart/New York, pp. 419–424 (1991).
Hans Steffen, BT Gattefossé No. 81, "Controlled Precipitation—A Method to Produce Small Drug Particles and to Increase Bioavailability", p. 45–53 (1988).

* cited by examiner

Primary Examiner—Gollamudi S. Kishore
Assistant Examiner—Amy E Pulliam
(74) Attorney, Agent, or Firm—George W. Johnston; William H. Epstein; Arthur D. Dawson (57) ABSTRACT

The present invention relates to a process for manufacturing a pulverous preparation of a submicron-sized biologically active compound comprising the steps of dissolving a biologically active compound under elevated pressure in a compressed gas, liquid or supercritical fluid containing a surface modifier; and rapidly expanding the compressed solution thereby precipitating the dissolved compound. An alternative process comprises dissolving the biologically active compound in compressed dimethylether, which may optionally contain a surface modifier; and spraying the compressed solution into an antisolvent phase, optionally containing a surface modifier, under vacuum, atmospheric pressure or elevated pressure. An optional third step involves converting the antisolvent phase into a pulverous preparation using conventional powder processing.

14 Claims, 3 Drawing Sheets